US006958476B2

(12) United States Patent
Davis et al.

(10) Patent No.: US 6,958,476 B2
(45) Date of Patent: Oct. 25, 2005

(54) METHODS TO IMPROVE RESOLUTION OF CROSS SECTIONED FEATURES CREATED USING AN ION BEAM

(75) Inventors: Todd J. Davis, Gilbert, AZ (US); Theodore Allen Paxton, Chandler, AZ (US)

(73) Assignee: ASML Netherlands B.V., Veldhoven (NL)

( * ) Notice: Subject to any disclaimer, the term of this patent is extended or adjusted under 35 U.S.C. 154(b) by 61 days.

(21) Appl. No.: 10/682,416

(22) Filed: Oct. 10, 2003

(65) Prior Publication Data

US 2005/0077467 A1     Apr. 14, 2005

(51) Int. Cl.⁷ ............................................ H01J 37/304
(52) U.S. Cl. ................. 250/307; 250/297; 250/492.21; 355/53; 216/59
(58) Field of Search .............................. 250/307, 297, 250/492.21; 355/53; 216/59

(56) References Cited

U.S. PATENT DOCUMENTS

| 4,788,117 | A   |   | 11/1988 | Cuthbert et al. |
|-----------|-----|---|---------|-----------------|
| 5,028,780 | A   |   | 7/1991  | Kaito et al. |
| 5,093,572 | A   |   | 3/1992  | Hosono |
| 5,739,898 | A   | * | 4/1998  | Ozawa et al. ................. 355/53 |
| 5,798,529 | A   |   | 8/1998  | Wagner |
| 6,350,390 | B1  | * | 2/2002  | Liu et al. ...................... 216/59 |
| 6,580,072 | B1  | * | 6/2003  | Chang et al. ............... 250/297 |

\* cited by examiner

Primary Examiner—Nikita Wells
Assistant Examiner—Zia R. Hashmi
(74) Attorney, Agent, or Firm—Pillsbury Winthrop Shaw Pittman, LLP

(57) ABSTRACT

Methods for creating a cross section of at least one feature located on a substrate are disclosed. The methods include coating the feature with a layer of contrast enhancing material, recoating the feature with a second material that is different from the contrast enhancing material, and milling the feature. The second material has substantially similar milling characteristics as the feature. The methods may further include creating an image of the feature and saving the image of the feature.

30 Claims, 7 Drawing Sheets

METHODS TO IMPROVE RESOLUTION OF CROSS SECTIONED FEATURES CREATED USING AN ION BEAM

BACKGROUND OF THE INVENTION

1. Field of the Invention

The present invention relates generally to the field of semiconductor device fabrication and more specifically to methods for examining features on a substrate.

2. Description of Related Art

The term "patterning structure" as here employed should be broadly interpreted as referring to a structure that can be used to endow an incoming radiation beam with a patterned cross section, corresponding to a pattern that is to be created in a target portion of the substrate; the term "light valve" can also be used in this context. Generally, the pattern will correspond to a particular functional layer in a device being created in the target portion, such as an integrated circuit or other device.

Examples of such patterning structure include a mask, a programmable mirror array, and a programmable LCD array. The concept of a mask is well known in lithography, and it includes mask types such as binary, alternating phase-shift, and attenuated phase-shift, as well as various hybrid mask types. Placement of such a mask in the radiation beam causes selective transmission (in the case of a transmissive mask) or reflection (in the case of a reflective mask) of the radiation impinging on the mask, according to the pattern on the mask. In the case of a mask, the support structure will generally be a mask table, which ensures that the mask can be held at a desired position in the incoming radiation beam, and that it can be moved relative to the beam if so desired.

An example of a programmable mirror array is a matrix-addressable surface having a viscoelastic control layer and a reflective surface. The basic principle behind such an apparatus is that, for example, addressed areas of the reflective surface reflect incident light as diffracted light, whereas unaddressed areas reflect incident light as undiffracted light. Using an appropriate filter, the said undiffracted light can be filtered out of the reflected beam, leaving only the diffracted light behind. In this manner, the beam becomes patterned according to the addressing pattern of the matrix-addressable surface. The required matrix addressing can be performed using a suitable electronic structure. More information on such mirror arrays can be gleaned, for example, from U.S. Pat. No. 5,296,891 and U.S. Pat. No. 5,523,193, which are incorporated herein by reference. In the case of a programmable mirror array, the said support structure may be embodied as a frame or table, for example, which may be fixed or movable as required.

An example of a programmable LCD array is given in U.S. Pat. No. 5,229,872, which is incorporated herein by reference. As above, the support structure in this case may be embodied as a frame or table, for example, which may be fixed or movable as required.

For purposes of simplicity, the rest of this text may, at certain locations, specifically direct itself to examples involving a mask and mask table. However, the general principles discussed in such instances should be seen in the broader context of the patterning structure as hereabove set forth.

A lithographic projection apparatus can be used, for example, in the manufacture of integrated circuits (ICs). In such a case, the patterning structure may generate a circuit pattern corresponding to an individual layer of the IC, and this pattern can be imaged onto a target portion, comprising one or more dies, for example, on a substrate (silicon wafer) that has been coated with a layer of radiation-sensitive material (resist). In general, a single wafer will contain a whole network of adjacent target portions that are successively irradiated via the projection system, one at a time. In current apparatus employing patterning by a mask on a mask table, a distinction can be made between two different types of machines.

In one type of lithographic projection apparatus, each target portion is irradiated by exposing the entire mask pattern onto the target portion at one time. Such an apparatus is commonly referred to as a wafer stepper. In an alternative apparatus, commonly referred to as a step-and-scan apparatus, each target portion is irradiated by progressively scanning the mask pattern under the projection beam in a given reference direction (the "scanning" direction) while synchronously scanning the substrate table parallel or anti-parallel to this direction. Because, in general, the projection system will have a magnification factor M (generally <1), the speed V at which the substrate table is scanned will be a factor M times that at which the mask table is scanned. More information with regard to lithographic devices as here described can be gleaned, for example, from U.S. Pat. No. 6,046,792, incorporated herein by reference.

In a manufacturing process using a lithographic projection apparatus, a pattern (e.g. in a mask) is imaged onto a substrate that is at least partially covered by a layer of radiation-sensitive material (resist). Prior to this imaging step, the substrate may undergo various procedures, such as priming, resist coating and a soft bake. After exposure, the substrate may be subjected to other procedures, such as a post-exposure bake (PEB), development, a hard bake and measurement/inspection of the imaged features. This array of procedures is used as a basis to pattern an individual layer of a device, e.g. an IC. Such a patterned layer may then undergo various processes such as etching, ion-implantation (doping), metallization, oxidation, chemo-mechanical polishing, etc., all intended to finish off an individual layer. If several layers are required, then the whole procedure, or a variant thereof, will have to be repeated for each new layer.

Eventually, an array of devices will be present on the substrate (wafer). These devices are then separated from one another by a technique such as dicing or sawing, whence the individual devices can be mounted on a carrier, connected to pins, etc. Further information regarding such processes can be obtained, for example, from the book "Microchip Fabrication: A Practical Guide to Semiconductor Processing", Third Edition, by Peter van Zant, McGraw Hill Publishing Co., 1997, ISBN 0-07-067250-4, incorporated herein by reference.

For the sake of simplicity, the projection system may hereinafter be referred to as the "lens"; however, this term should be broadly interpreted as encompassing various types of projection system, including refractive optics, reflective optics, and catadioptric systems, for example. The radiation system may also include components operating according to any of these design types for directing, shaping or controlling the projection beam of radiation, and such components may also be referred to below, collectively or singularly, as a "lens". Further, the lithographic apparatus may be of a type having two or more substrate tables (and/or two or more mask tables). In such "multiple stage" devices, the additional tables may be used in parallel, or preparatory steps may be carried out on one or more tables while one or more other tables are being used for exposures. Twin stage lithographic apparatus are described, for example, in U.S. Pat. No. 5,969,441 and WO 98/40791, incorporated herein by reference.

Semiconductor manufacturers generally examine features on a substrate to determine whether the desired feature conforms with a specification for, for example, a semiconductor device, or to calibrate the lithographic apparatus. In doing so, cross sections of the features are created for imaging evaluation, feature evaluation, and even for feature modeling. The traditional method for creating cross sections of features requires the sample to be cleaved into pieces. Such methods may take a long time, and are thus costly because in many cases, manufacturing must be delayed pending results of the evaluation of the cross section.

BRIEF SUMMARY OF THE INVENTION

It is therefore an aspect of an embodiment of the present invention to provide methods for creating a cross section of a feature that overcome the deficiencies of the current method.

As such, the present invention provides methods for creating a cross section of at least one feature located on a substrate. In one embodiment, the method includes coating the feature with a layer of contrast enhancing material, recoating the feature with a second material that is different from the contrast enhancing material and has substantially similar milling characteristics as the feature, and milling the feature. The feature may include resist, dielectric, or conducting material.

In another embodiment, the method includes patterning the substrate with a feature including a first resist material, coating the feature with a layer of conducting material, recoating the feature with a second resist material, and milling the feature.

In a further embodiment, the method includes patterning the substrate with a feature including a first dielectric material, coating the feature with a layer of conducting material, recoating the feature with a second dielectric material, and milling the feature.

In still another embodiment, the method includes patterning the substrate with a feature including a first conducting material, coating the feature with a later of dielectric material, recoating the feature with a second conducting material, and milling the feature.

BRIEF DESCRIPTION OF THE DRAWINGS

Aspects of the invention are shown in the drawings, which form part of this original disclosure. Embodiments of the invention will be described in conjunction with the following drawings, in which.

DETAILED DESCRIPTION OF THE INVENTION

Figure 1:
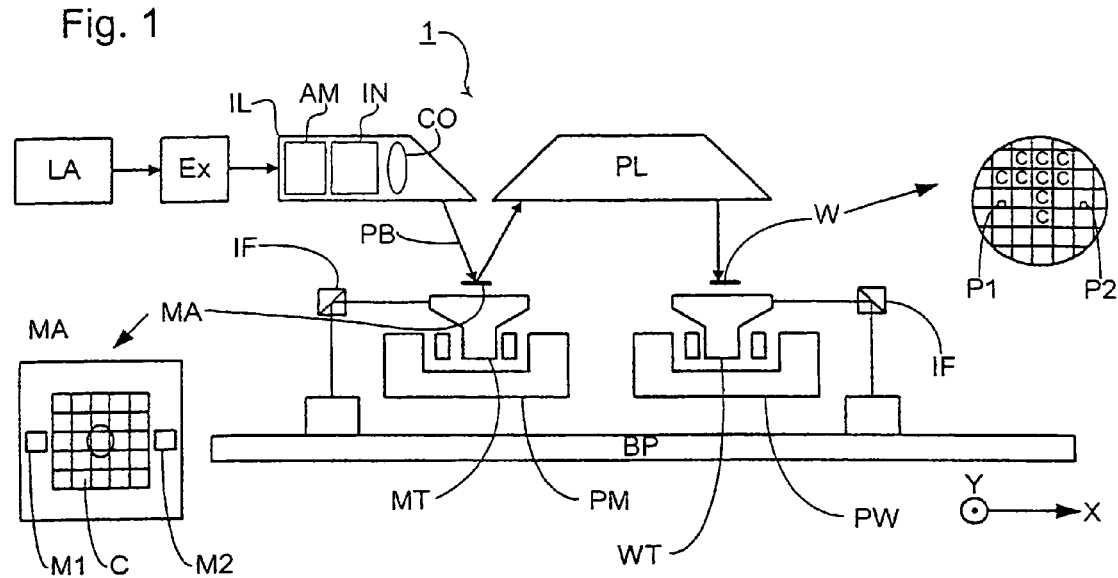
FIG. 1 is a schematic diagram of a lithographic projection apparatus used to manufacture semiconductor devices that are subjected to the methods of at least one embodiment of the present invention.

FIG. 1 schematically depicts a lithographic projection apparatus 1 that may be used to manufacture devices as used in accordance with embodiments of the invention. The apparatus 1 includes a radiation system Ex, IL, for supplying a projection beam PB of radiation (e.g. EUV), which in this particular case also comprises a radiation source LA; a first object table (mask table) MT provided with a mask holder for holding a mask MA (e.g. a reticle), and connected to a first positioning structure for accurately positioning the mask with respect to item PL; a second object table (substrate table) WT provided with a substrate holder for holding a substrate W (e.g. a resist-coated silicon wafer), and connected to a second positioning structure for accurately positioning the substrate with respect to item PL; and a projection system ("lens") PL (e.g. a refractive or catadioptric system or a reflective system) for imaging an irradiated portion of the mask MA onto a target portion C (e.g. comprising one or more dies) of the substrate W.

As here depicted, the apparatus 1 is of a reflective type (i.e. has a reflective mask). However, in general, it may also be of a transmissive type, for example, with a transmissive mask. Alternatively, the apparatus 1 may employ another kind of patterning structure, such as a programmable mirror array of a type as referred to above.

The source LA (e.g. an undulator or wiggler provided around the path of an electron beam in a storage ring or synchrotron, a laser, a mercury lamp, a plasma dicharge device, etc.) produces a beam of radiation. This beam is fed into an illumination system (illuminator) IL, either directly or after having a traversed conditioning structure, such as a beam expander Ex, for example. The illuminator IL may comprise an adjusting structure AM for setting the outer and/or inner radial extent (commonly referred to as σ-outer and σ-inner, respectively) of the intensity distribution in the beam. In addition, it will generally comprise various other components, such as an integrator IN and a condenser CO. In this way, the beam PB reflected by the mask MA has a desired uniformity and intensity distribution in its cross-section.

It should be noted with regard to FIG. 1 that the source LA may be within the housing of the lithographic projection apparatus 1 (as is often the case when the source LA is a mercury lamp, for example), but that it may also be remote from the lithographic projection apparatus 1, the radiation beam which it produces being led into the apparatus 1 (e.g. with the aid of suitable directing mirrors, optical fibers, or other waveguides). This latter scenario is often the case when the source LA is an excimer laser.

The beam PB subsequently intercepts the mask MA, which is held on a mask table MT. After being selectively reflected by the mask MA, the beam PB passes through the lens PL, which focuses the beam PB onto a target portion C of the substrate W. With the aid of the second positioning structure (and interferometric measuring structure IF), the substrate table WT can be moved accurately, e.g. so as to position different target portions C in the path of the beam PB. Similarly, the first positioning structure can be used to accurately position the mask MA with respect to the path of the beam PB, e.g. after mechanical retrieval of the mask MA from a mask library, or during a scan. In general, movement of the object tables MT, WT will be realized with the aid of a long-stroke module (course positioning) and a short-stroke module (fine positioning), which are not explicitly depicted in FIG. 1. However, in the case of a wafer stepper (as opposed to a step-and-scan apparatus) the mask table MT may just be connected to a short stroke actuator, or may be fixed.

The depicted apparatus 1 can be used in two different modes. First, in step mode, the mask table MT is kept essentially stationary, and an entire mask image is projected in one go (i.e. a single "flash") onto a target portion C. The substrate table WT is then shifted in the x and/or y directions so that a different target portion C can be irradiated by the beam PB. Second, in scan mode, essentially the same scenario applies, except that a given target portion C is not exposed in a single "flash". Instead, the mask table MT is movable in a given direction (the so-called "scan direction", e.g. the y direction) with a speed v, so that the projection beam PB is caused to scan over a mask image; concurrently, the substrate table WT is simultaneously moved in the same or opposite direction at a speed V=Mv, in which M is the magnification of the lens PL (typically, M=¼ or ⅕). In this manner, a relatively large target portion C can be exposed, without having to compromise on resolution.

Additional known processes, including but not limited to etching, ion-implantation (doping), metallization, oxidation, and chemo-mechanical polishing, may be used to create features on the substrate. For example, metal and metal oxide features may be defined by an etch process that transfers the resist pattern to a substrate.

Regardless of the specific method to manufacture the device, samples must be routinely evaluated to ensure that the end product includes the desired features and properties. That is, the process must be routinely qualified. Such inspections may also be used to qualify feature modeling and to optimize the process using a line pattern that does not necessarily include circuitry for a device. It is also contemplated that information gained from inspection may be used to calibrate in line metrology, such as scatterometry tools.

Alternative methods to cleaving have been developed. One such method uses a focused ion beam ("FIB") tool to create cross sections of features in a method commonly referred to as "milling." This method uses the FIB tool to cut a hole or a trough into the device such that the cross section of the feature can be viewed with a powerful microscope, such as a scanning electron microscope ("SEM"). Because the features are small and are sometimes difficult to distinguish under an SEM, the FIB tool, or separate sputtering tool, may be used to locally coat the feature of interest with a thin layer of a contrast enhancing material prior to milling. The coating provides contrast so that the outline of the feature may be discerned. The SEM may be used to create and save an image of the feature so that the appropriate analysis can be completed.

Figure 9:
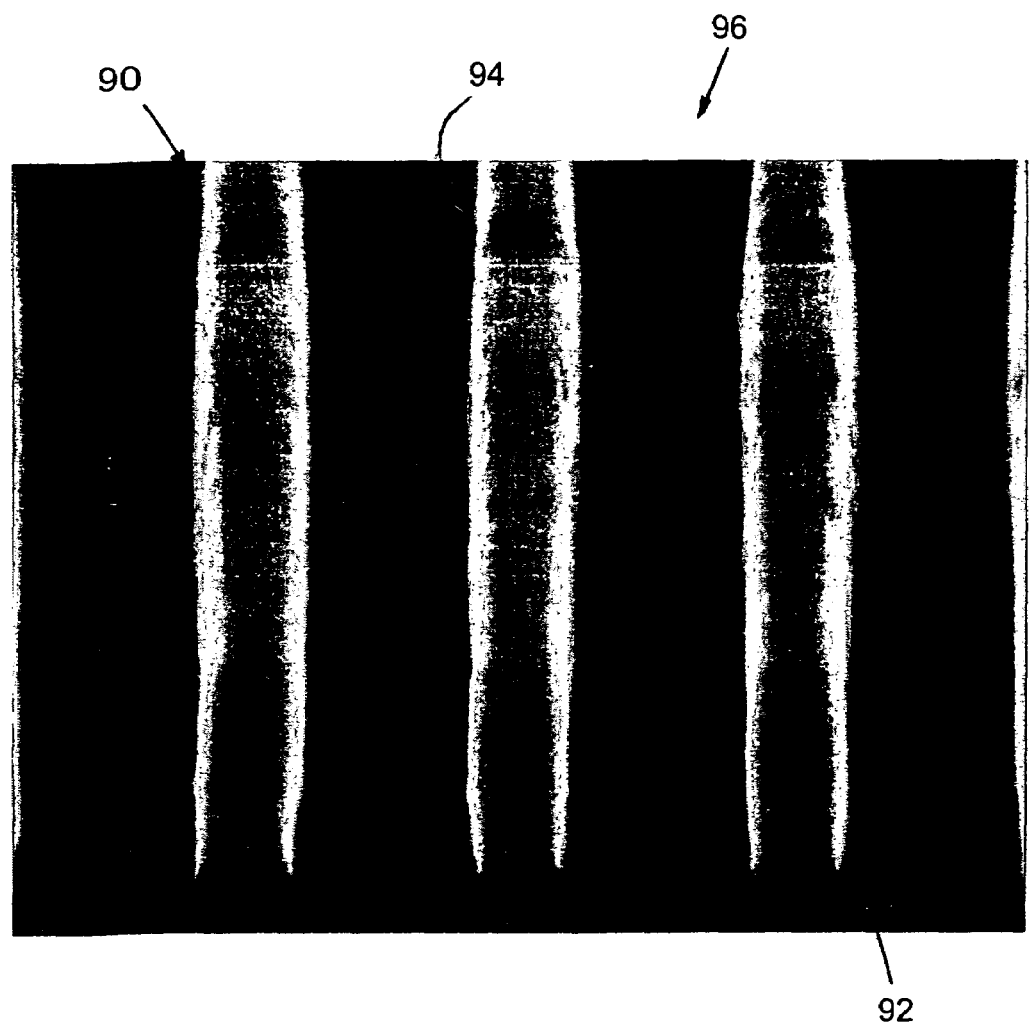
FIG. 9 (Related Art) is representation of a scanning electron micrograph of a cross section of a feature prepared from a method of related art.

Unfortunately, the milling process known in the art does not result in a clean or sharp cross section for all materials. This is because feature deformation is inherent to FIB milling at the interface of dissimilar materials. Thus, there will be distortion at the interface of the feature and any voids and at the interface of the feature and any non-similar material applied on top of the feature. As a result, as shown in FIG. 9 (Related Art), an upper portion 90, lower portion 92, and edges 94 of a feature 96 are not distinct. The problem is most apparent as the features decrease in size and increase in pitch.

As features on wafers get progressively smaller, the area on the feature that is deformed by the ion beam is a larger percentage of the entire feature. Thus, the method for creating cross sections of features must minimize the deformation of the features so that accurate evaluations can be made.

Figure 2:
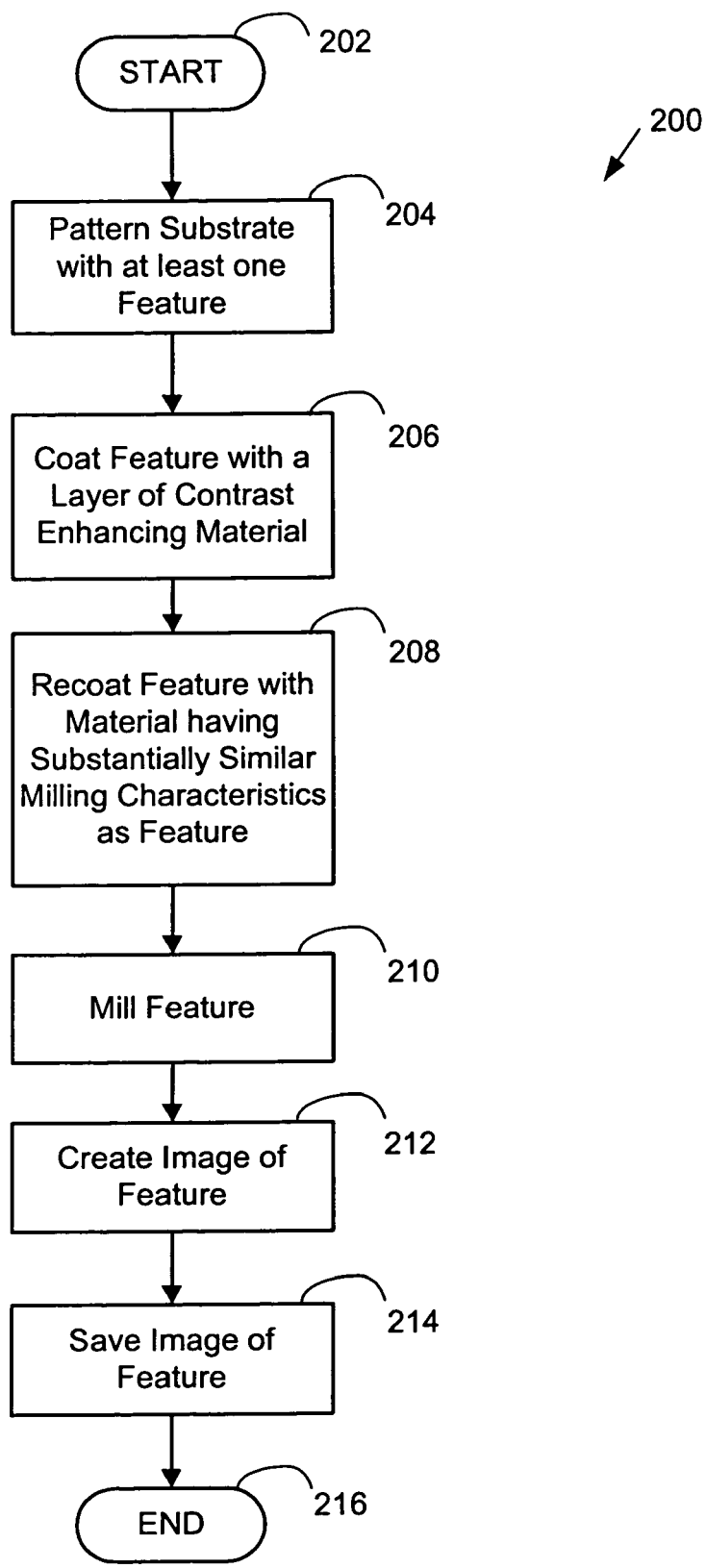
FIG. 2 is a flow diagram of at least one embodiment of methods of the present invention for creating a cross section of a feature of a device.
Figure 3:
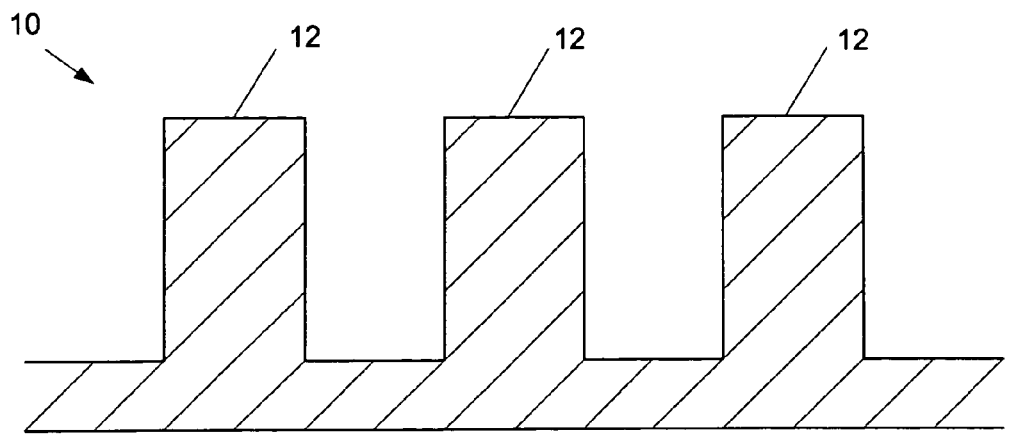
FIG. 3 is a schematic of a cross section of at least one feature after it has been patterned on a wafer in accordance with at least one embodiment of the present invention.

FIG. 2 is a flow diagram of at least one embodiment of the present invention of methods for creating a cross section of at least one feature. FIG. 2 illustrates a method 200 that starts at 202. At 204, the substrate, which may include, for example, wafer W, is patterned with at least one feature. The feature may include, but is not limited to, resist, dielectric, or conducting material. Any apparatus known in the art may be used to pattern the substrate. FIG. 3 illustrates a cross section of a portion of a substrate with a feature.

Figure 4:
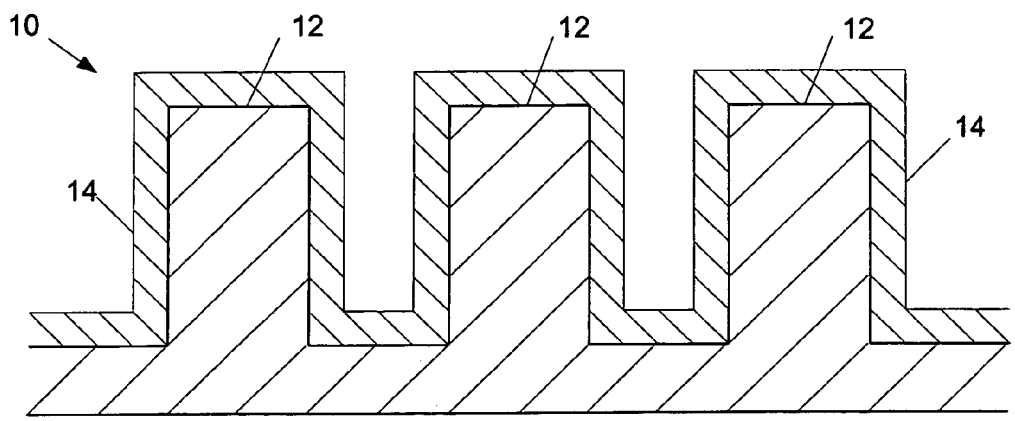
FIG. 4 is a schematic of the cross section of the feature shown in FIG. 3 after it has been coated with a layer of contrast enhancing material in accordance with at least one embodiment of the present invention.

Returning to FIG. 2, at 206, at least one feature is coated with a layer of contrast enhancing material. FIG. 4 illustrates the result of this process, showing the feature 12 coated with a layer of contrast enhancing material 14. As shown in FIG. 4, the deposited contrast enhancing material 14 is preferably conformal, i.e., the contrast enhancing material 14 conforms to the patterned feature 12. This way, an outline or profile of the feature 12 is created. The contrast enhancing material 14 improves the image contrast of a scanning electron microscope ("SEM") that may be used later in the method, as explained below. An ion beam tool, such as a focused ion beam ("FIB") tool, of a known design may be used to coat the feature 12 with the contrast enhancing material 14. Alternatively, a separate sputtering tool, or other deposition device, of a known design may be used to coat the feature 12 with the contrast enhancing material 14.

In the case of imaging a layer of resist or dielectric material, a conductor such as a metal will generally provide good contrast, particularly when using an SEM. For example, when the feature 12 includes resist material, the contrast enhancing material 14 may be platinum or gold or any other material that enhances contrast. Likewise, when imaging a metallic, or conducting, feature, an oxide or other dielectric may be preferable. The layer of contrast enhancing material 14 typically includes a thickness of about 25 to about 50 angstroms. This provides a layer that is thick enough to be detected by the SEM but not excessively thick to create undue expense or problems. For example, as would be recognized by one of ordinary skill in the art, if the layer of contrast enhancing material is too thick, the effectiveness of the resultant outline or profile of the feature will be diminished. Also, the contrast enhancing layer may adversely impact the milling process if the layer is too thick.

Returning to FIG. 2, the method proceeds to 208, where the feature is recoated with a second material that is different from the contrast enhancing material. The second material should have substantially similar milling characteristics as the feature itself. The second material used to recoat the feature may be the same material that was used to create the feature, or any material with similar milling characteristics such that any deformation created due to an interface of dissimilar materials is minimized. Preferably, the second material is the same as the material that was used to create the feature. For example, if the feature includes resist material, the second material will preferably include the same resist material or a material with substantially similar milling characteristics.

Figure 5:
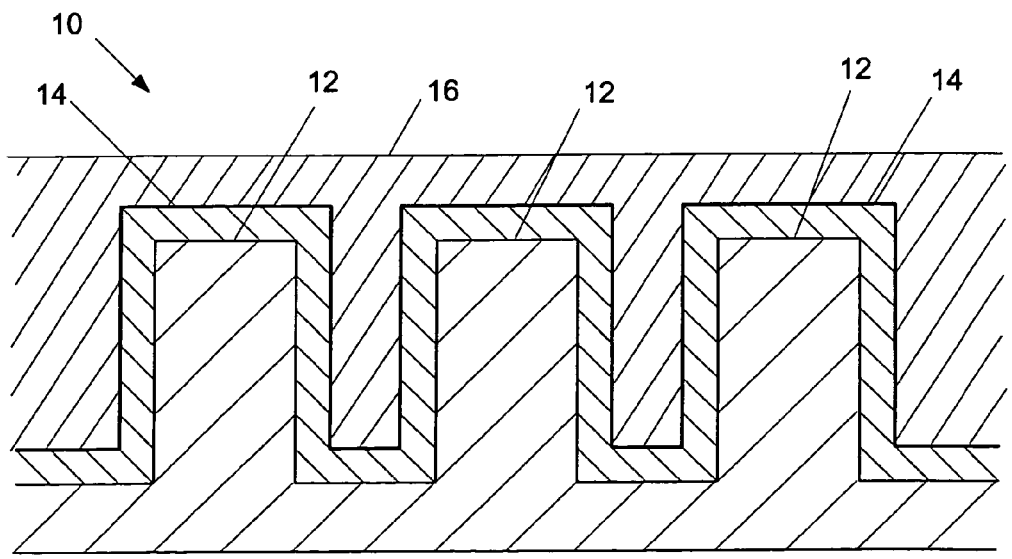
FIG. 5 is a schematic of the cross section of the feature shown in FIG. 4 after it has been recoated with a material having similar milling characteristics as the feature in accordance with at least one embodiment of the present invention.

As shown in FIG. 5, enough material should be deposited to fill any voids that are present in the feature 12 and to cover the contrast enhancing material 14. A spin coating process may be used for recoating the feature 12. Because the second material 16 should be applied such that it fills voids present in the target area of the substrate, thereby yielding a uniform coating, the spin coater may, in some cases, be operated at relatively low speeds. The appropriate speed will depend on the second material 16 being used, but is generally less than about 1000 rpm. One of ordinary skill in the art would recognize that the optimum speed will depend on the viscosity of the second material 16. It is contemplated that a wafer track may be used to recoat the feature 12 with the second material 16. As would be recognized by one of ordinary skill in the art, any material depositing process may be used to uniformly coat any feature that has been patterned on a substrate.

Returning to FIG. 2, the feature is then milled to create the cross section at 210. The ion beam tool may be used to mill either a hole or a trough in the feature. This creates a cross section of the feature. One of ordinary skill in the art would recognize that a precursor gas may be used during milling to enhance the selectivity of organic materials. This allows the milling process to proceed faster, as compared to milling without the precursor gas.

In FIG. 2, at 212, an image of the feature may be created using, for example, an SEM. The image may also be saved at 214 for further analysis. The method ends at 216.

EXAMPLE

The following example is intended to be illustrative of at least one embodiment of the method 200 of FIG. 2 and is not intended to be limiting in any way.

At 204, the apparatus 1 is used to coat the wafer W with a bottom anti reflective coating ("BARC") at a desired thickness. The BARC coated wafer is then baked. The BARC coated wafer is further coated with resist material at a desired thickness, and then baked. The wafer is then exposed using a stepper/scanner portion and the mask MA of the apparatus 1. For chemically amplified resist, the exposed wafer is baked, then developed.

At 206, the developed wafer is loaded into a dual beam system that has the capability of coating the wafer with platinum. The wafer is tilted to about 52 degrees, normal to an ion column within the dual beam system. The area of the wafer to be coated is located by the operator and the coordinates are saved. A platinum injector is inserted into the system and then opened. An ion beam, set at 1000 pA and 2 k magnification, is turned on for about 40 seconds. After the ion beam is turned off, the platinum injector is retracted, and the wafer is unloaded from the dual beam system.

At 208, the wafer is loaded back into the apparatus 1, or any device that includes a wafer track. The wafer is then coated with the same resist or BARC material that was used at 204. The wafer track is operated at a reduced spin speed, about 600 rpm, such that no voids are present between features of interest. As would be recognized by one of ordinary skill in the art, the optimum spin speed will vary by material. The wafer may then be baked, but as would be recognized by one of ordinary skill in the art, it is not required that the wafer be baked at this point in the process. The wafer is then unloaded from the apparatus 1.

At 210, the wafer is loaded back into the dual beam system. Once loaded into the dual beam system, the wafer is tilted to about 52 degrees and a eucentric height is set. An ion beam is set to a milling current of less than about 20 pA. One of ordinary skill in the art would recognize that the proper milling current is highly dependent on the substrate. The ion beam is aligned with an electron beam and the feature of interest is located with the electron beam. The ion beam is set to a milling magnification. A precursor gas injector is inserted into the dual beam system. A fast image scan is then performed with the ion beam, and a milling recipe is selected by the operator. A milling window is then drawn and a milling sequence started. The operator may choose to repeat the fast image scan, choose the milling recipe, draw the milling window, and start another milling sequence until an acceptable cross section surface is created.

Once an acceptable cross section surface is created, the dual beam system is switched to the electron beam function, at 212. A desired magnification is set and the operator may adjust the focus and stigmation, if required. The cross section is scanned into an image at the desired resolution and scan rate using the electron beam. At 214, the image is saved using the dual beam system.

Figure 6:
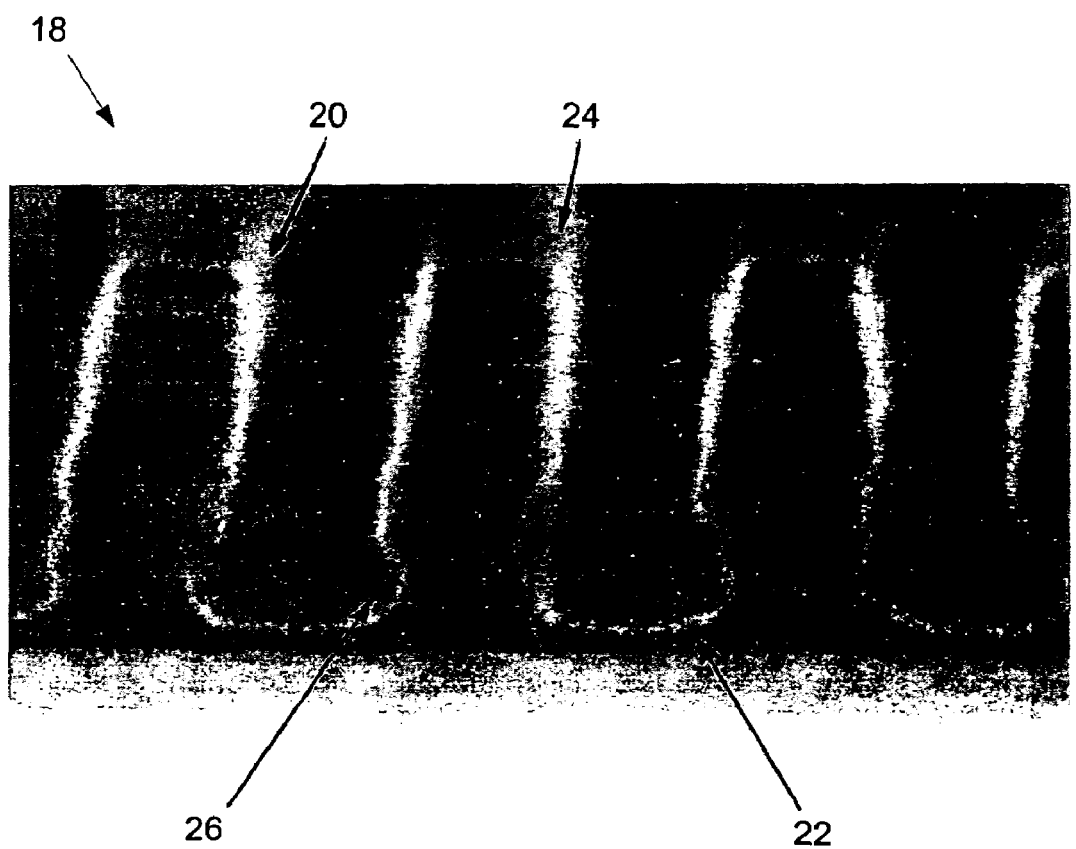
FIG. 6 is representation of a scanning electron micrograph of a cross section of a feature in accordance with at least one embodiment of the present invention.

FIG. 6 shows an example of a resulting image 18. As shown in FIG. 6, high portions 20 and low portions 22 of a feature 24 are clearly identifiable. Also, irregularities 26, such as undercutting, in the feature 24 can be clearly identified.

Figure 7:
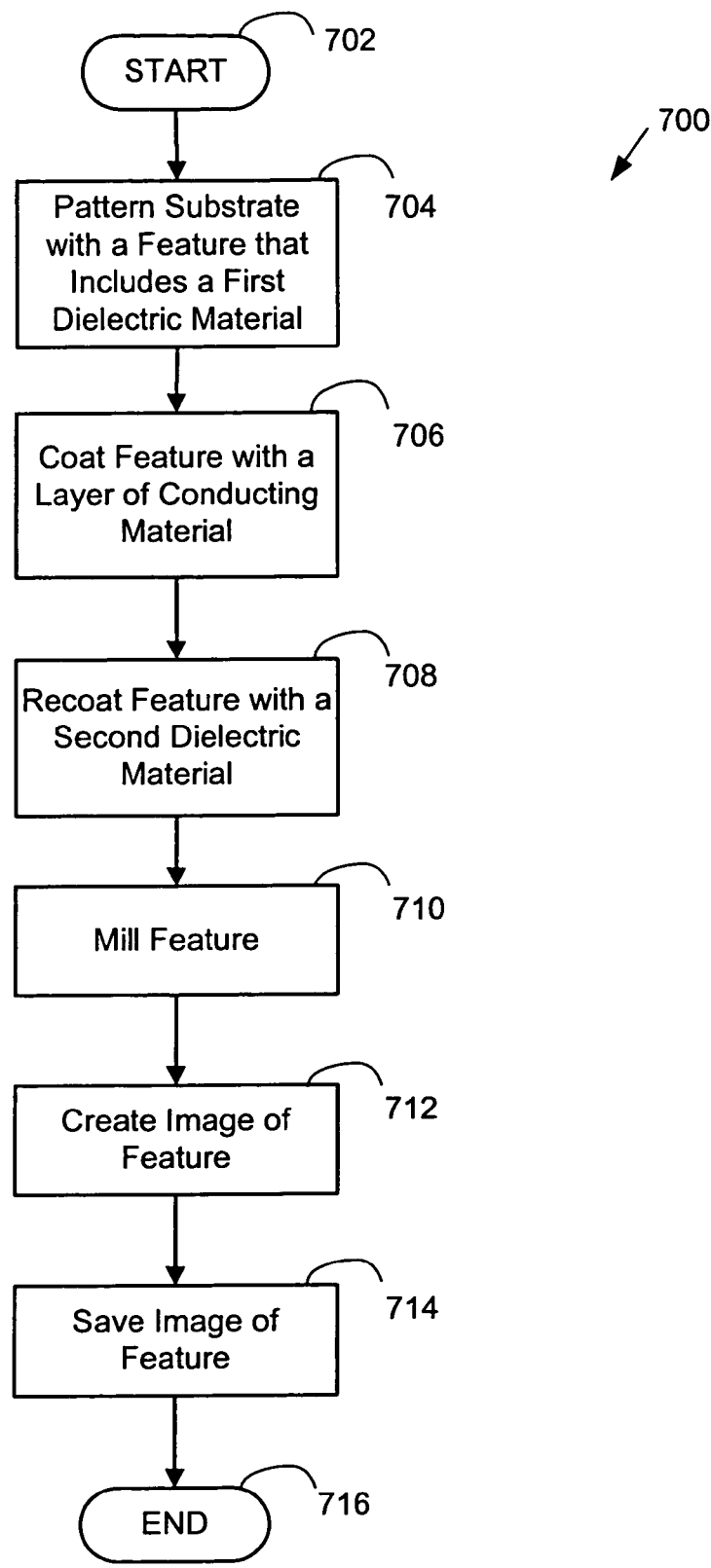
FIG. 7 is a flow diagram of at least one embodiment of another method of the present invention for creating a cross section of a feature of a device.

FIG. 7 is a flow diagram that illustrates at least one additional embodiment of the invention. A method for creating a cross section of at least one feature located on a substrate, such as the wafer W, is shown generally at 700. The method 700 starts at 702. At 704, the substrate is patterned with a feature including a dielectric material. Any apparatus known in the art may be used to pattern the substrate. At 706, the feature within the selected target area for inspection is coated with a layer of conducting material. The ion beam tool may be utilized to coat the feature. The conducting material is preferably platinum or gold, but may be any conducting material that provides contrast when viewing the coated feature under an SEM. At 708, the feature is recoated with a second dielectric material. Preferably, the second dielectric material used at 708 has similar milling characteristics as the feature. It is contemplated that the second dielectric material may be the same material used to create the feature. The feature is then milled at 710 with the ion beam tool. An image is created of the feature at 712. The image is preferably created by an SEM, although any suitable microscope or image enhancing device may be used. The image may be saved at 714 so that further analysis can be completed on the image at a later time. The method ends at 716.

Figure 8:
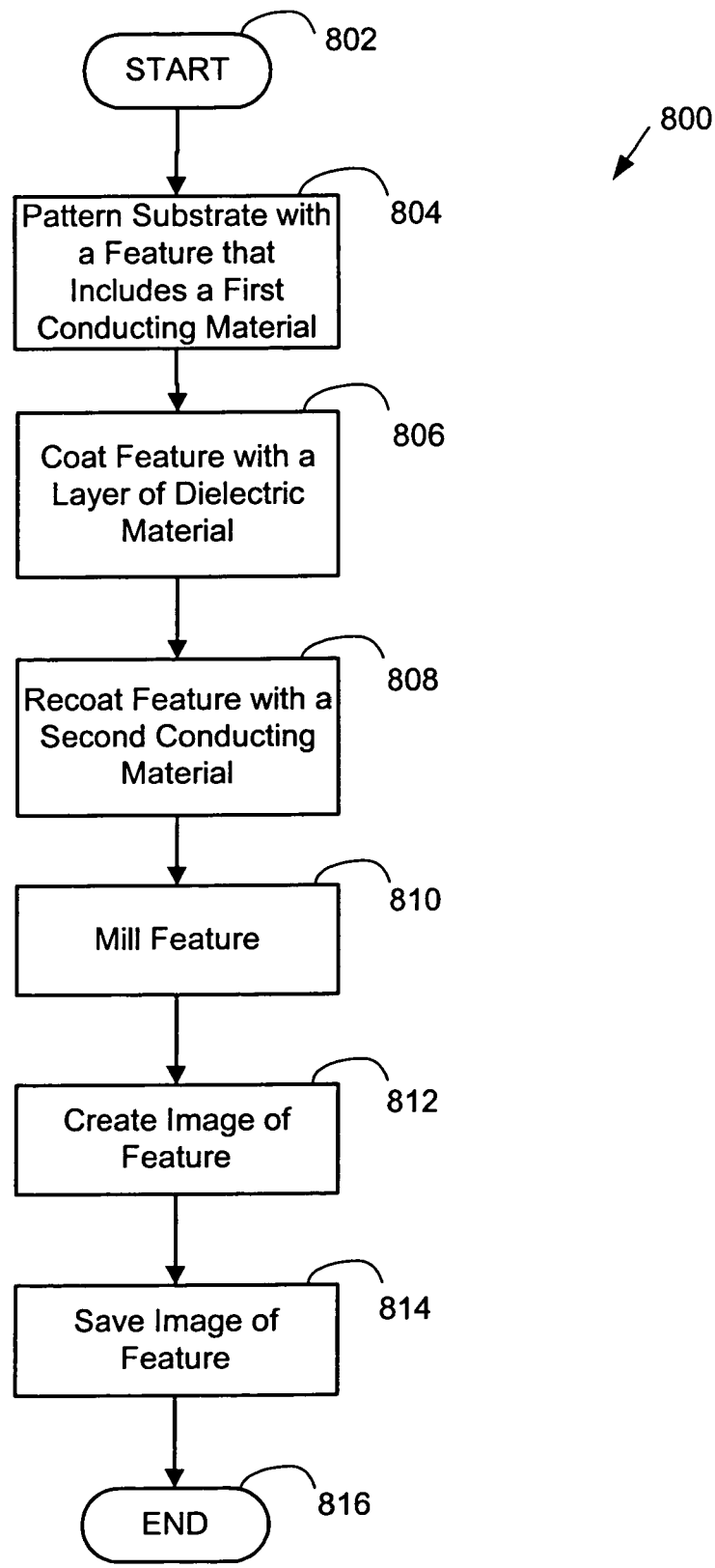
FIG. 8 is a flow diagram of at least one embodiment of a further method of the present invention for creating a cross section of a feature of a device.

FIG. 8 is a flow diagram that illustrates at least one further embodiment of the invention. A method for creating a cross section of at least one feature located on a substrate is shown generally at 800. The method 800 starts at 802. At 804, the substrate is patterned with a feature composed of a conducting material. Any apparatus known in the art may be used to pattern the substrate. At 806, the feature within the selected target area for inspection is coated with a layer of dielectric material. The ion beam tool may be utilized to perform this step. The dielectric material is preferably a metal oxide, but may be any dielectric material that provides contrast when viewing the coated feature under an SEM. At 808, the substrate is recoated with a second conducting material. Preferably, the second conducting material used at 808 has similar milling characteristics as the feature. It is contemplated that the second conducting material may be the same material used to create the feature. The feature is then milled at 810. Preferably, the ion beam tool is used to mill the feature. An image may be created of the feature at 812. The image is preferably created by an SEM. The image may be saved at 814 so that further analysis may be completed on the image at a later time. The method 800 ends at 816.

One aspect of the aforementioned embodiments of the present invention is that the ion beam that is used to mill the feature does not distort the feature during milling. This is important as the size of the feature decreases, particularly when the feature is less than about 180 nanometers in size.

While embodiments of the invention have been shown and described, they are not intended to be limiting in any respect. To the contrary, the invention is intended to encompass all variations and modifications within the spirit and scope of the appended claims.

What is claimed is:

1. A method for creating a cross section of at least one feature located on a substrate, the method comprising:
   coating the feature with a layer of contrast enhancing material;
   recoating the feature with a second material different from the contrast enhancing material, the second material having substantially similar milling characteristics as the feature; and
   milling the feature.

2. The method of claim 1, wherein the feature comprises resist material.

3. The method of claim 1, wherein the feature comprises dielectric material.

4. The method of claim 1, wherein the feature comprises conducting material.

5. The method of claim 1, wherein the layer of contrast enhancing material comprises a thickness of about 25–50 angstroms.

6. The method of claim 1, wherein coating the feature with the layer of contrast enhancing material comprises utilizing an ion beam tool to deposit the contrast enhancing material.

7. The method of claim 1, wherein recoating the feature comprises utilizing a spin coat machine to recoat the feature with the second material.

8. The method of claim 7, further comprising spinning the substrate at a speed of less than about 1000 rpm.

9. The method of claim 1, wherein milling the feature comprises utilizing an ion beam to mill the feature.

10. The method of claim 10, wherein milling the feature comprises using a precursor gas.

11. The method of claim 1, further comprising creating an image of the feature.

12. The method of claim 11, wherein creating the image of the feature comprises utilizing a scanning electron microscope to create the image.

13. The method of claim 12, further comprising saving the image of the feature.

14. A method for creating a cross section of at least one feature located on a substrate, the method comprising:
   patterning the substrate with the feature, the feature comprising a first resist material;
   coating the feature with a layer of conducting material;
   recoating the feature with a second resist material; and
   milling the feature.

15. The method of claim 14, wherein the conducting material comprises platinum.

16. The method of claim 14, wherein the conducting material comprises gold.

17. The method of claim 14, wherein the first resist material and the second resist material comprise the same material.

18. The method of claim 14, wherein the first resist material and the second resist material comprise different materials having substantially similar milling characteristics.

19. The method of claim 14, further comprising creating an image of the feature.

20. A method for creating a cross section of at least one feature located on a substrate, the method comprising:
   patterning the substrate with the feature, the feature comprising a first dielectric material;
   coating the feature with a layer of conducting material;
   recoating the feature with a second dielectric material; and
   milling the feature.

21. The method of claim 20, wherein the conducting material comprises platinum.

22. The method of claim 20, wherein the conducting material comprises gold.

23. The method of claim 20, wherein the first dielectric material and the second dielectric material comprise the same material.

24. The method of claim 20, wherein the first dielectric material and the second dielectric material comprise different materials having substantially similar milling characteristics.

25. The method of claim 20, further comprising creating an image of the feature.

26. A method for creating a cross section of at least one feature located on a substrate, the method comprising:
   patterning the substrate with the feature, the feature comprising a first conducting material;
   coating the feature with a layer of dielectric material;
   recoating the feature with a second conducting material; and
   milling the feature.

27. The method of claim 26, wherein the non-conducting material comprises metal oxide.

28. The method of claim 26, further comprising creating an image of the feature.

29. The method of claim 26, wherein the first conducting material and the second conducting material comprise the same material.

30. The method of claim 26, wherein the first conducting material and the second conducting material comprise different materials having substantially similar milling characteristics.

* * * * *